(12) United States Patent
Park et al.

(10) Patent No.: US 7,630,071 B2
(45) Date of Patent: Dec. 8, 2009

(54) INSPECTING APPARATUS FOR GLASS SUBSTRATE

(75) Inventors: Jungho Park, Seoul (KR); Sooyoun Kim, Gyeonggi-do (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 12/003,629

(22) Filed: Dec. 28, 2007

(65) Prior Publication Data
US 2008/0239302 A1 Oct. 2, 2008

(30) Foreign Application Priority Data
Mar. 28, 2007 (KR) .................... 10-2007-0030285

(51) Int. Cl.
*G01N 21/00* (2006.01)
(52) U.S. Cl. .................. 356/239.1; 356/237.2
(58) Field of Classification Search ............. 356/239.1, 356/239.2, 239.3, 237.2, 237.5
See application file for complete search history.

(56) References Cited
U.S. PATENT DOCUMENTS 3,792,930 A * 2/1974 Obenreder .................. 356/445
5,691,811 A * 11/1997 Kihira ...................... 356/239.1
7,215,418 B2 * 5/2007 Gahagan et al. .......... 356/237.2
2004/0174519 A1 * 9/2004 Gahagan et al. .......... 356/239.1
2008/0055606 A1 * 3/2008 Inoue et al. ................. 356/491

* cited by examiner

*Primary Examiner*—Roy Punnoose
(74) *Attorney, Agent, or Firm*—Holland & Knight LLP

(57) ABSTRACT

An inspecting apparatus for a glass substrate detects blurs of a green color filter layer, a blue color filter layer, a column spacer layer, a pixel layer of a thin film transistor, or the like, which are generally hardly inspected. The inspecting apparatus for a glass substrate includes: a first illumination unit supplying reflective light to a surface of the substrate to inspect whether the surface of the substrate is defective or not; a second illumination unit supplying transmissive light from a rear side of the substrate to inspect whether the interior of the substrate is defective or not; a latticed rear plate provided on a rear surface of the substrate; and a driving interferometer system generating a phase difference of light by driving such that a driving guide is moved along the rear plate or the rear plate itself is moved.

16 Claims, 8 Drawing Sheets

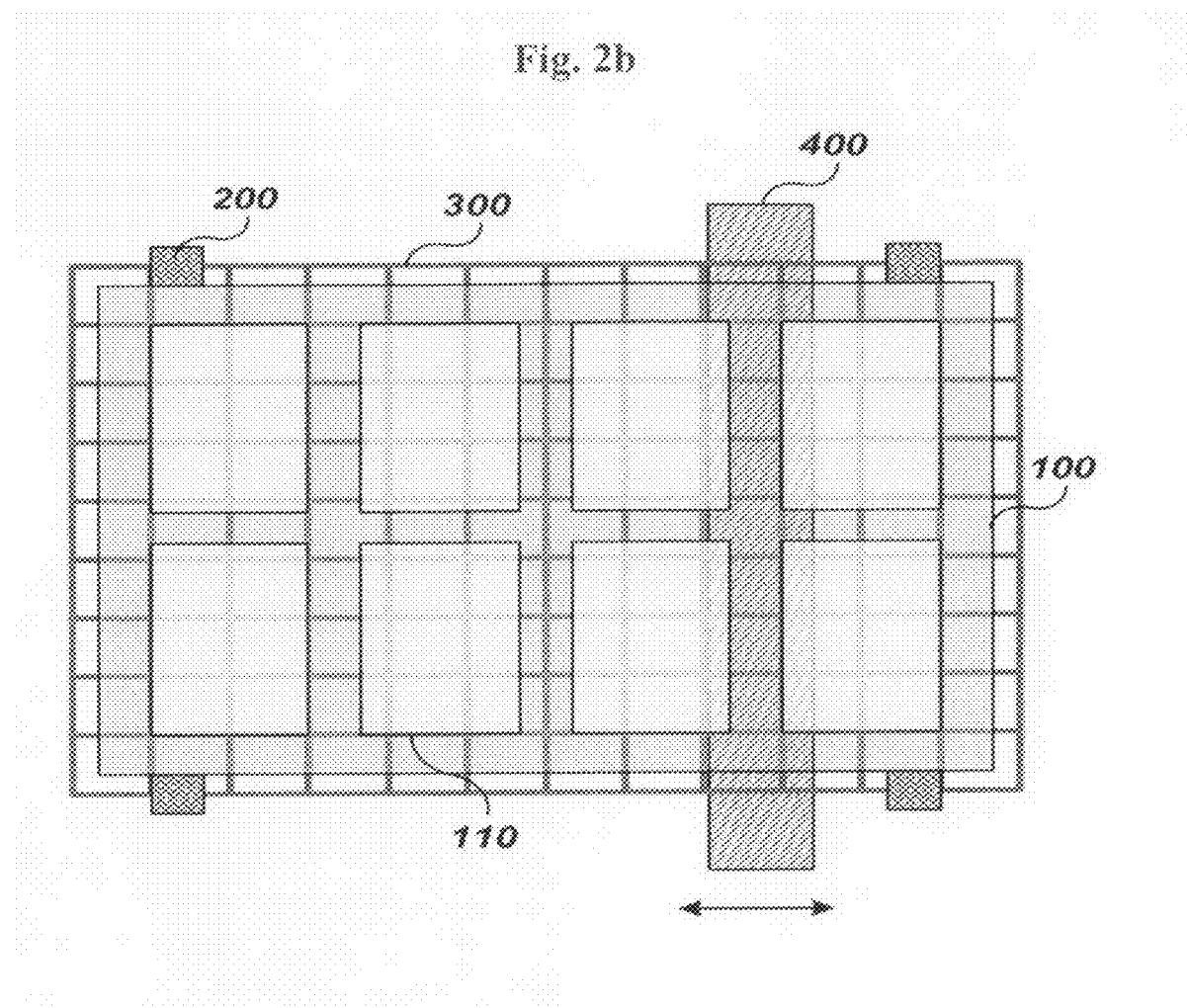

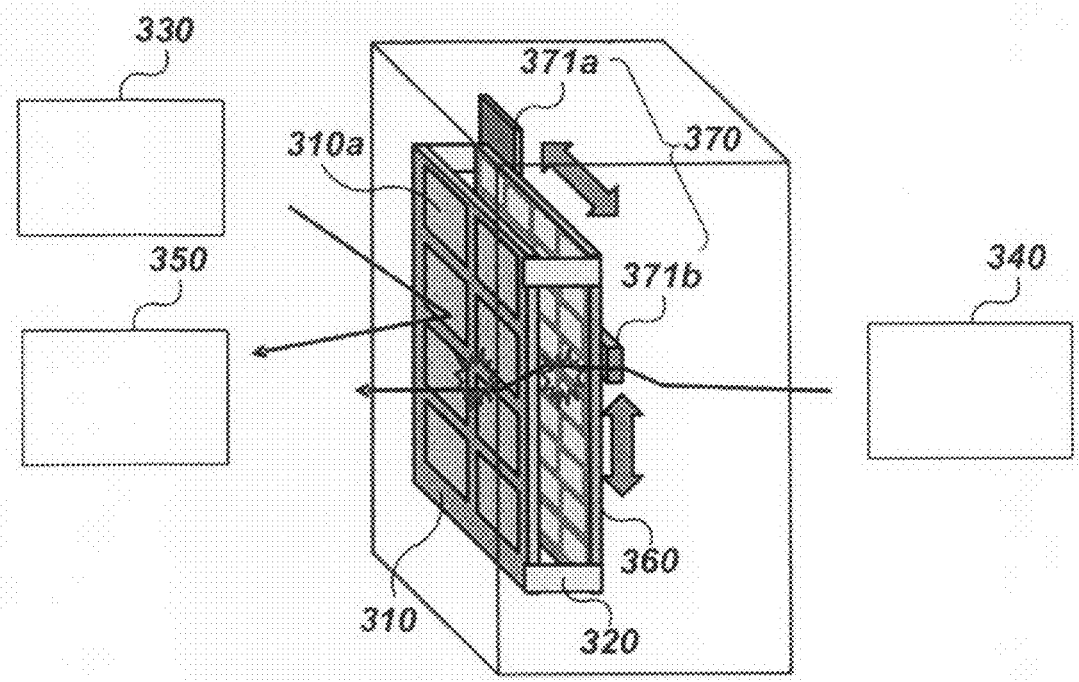

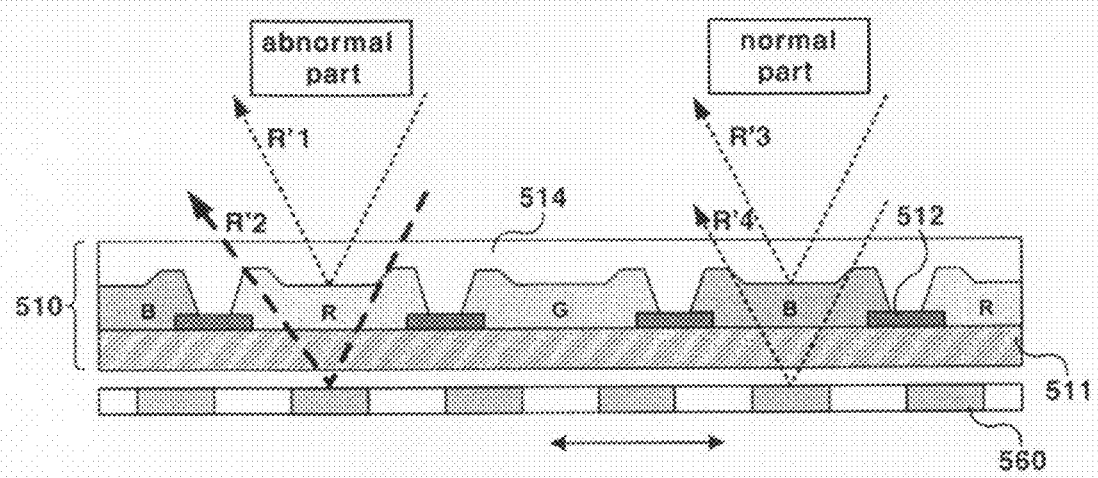

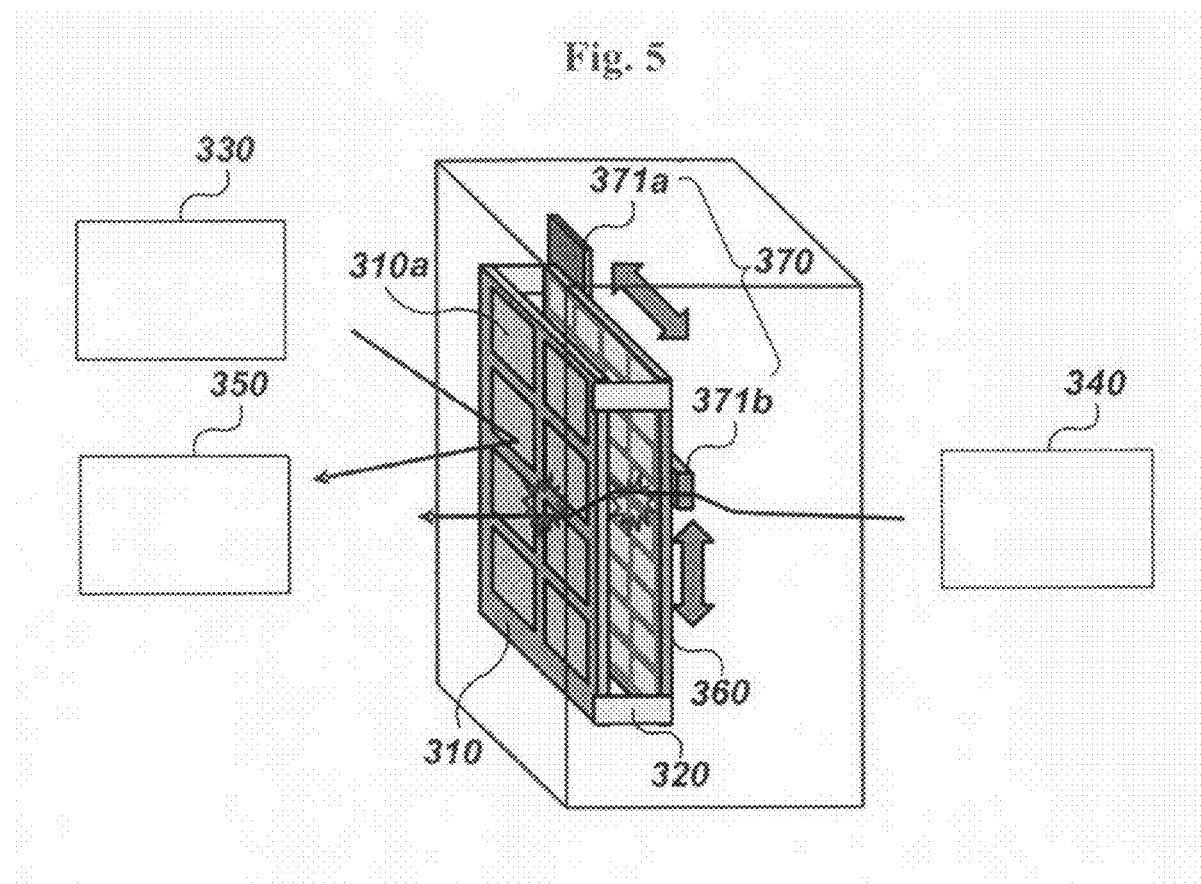

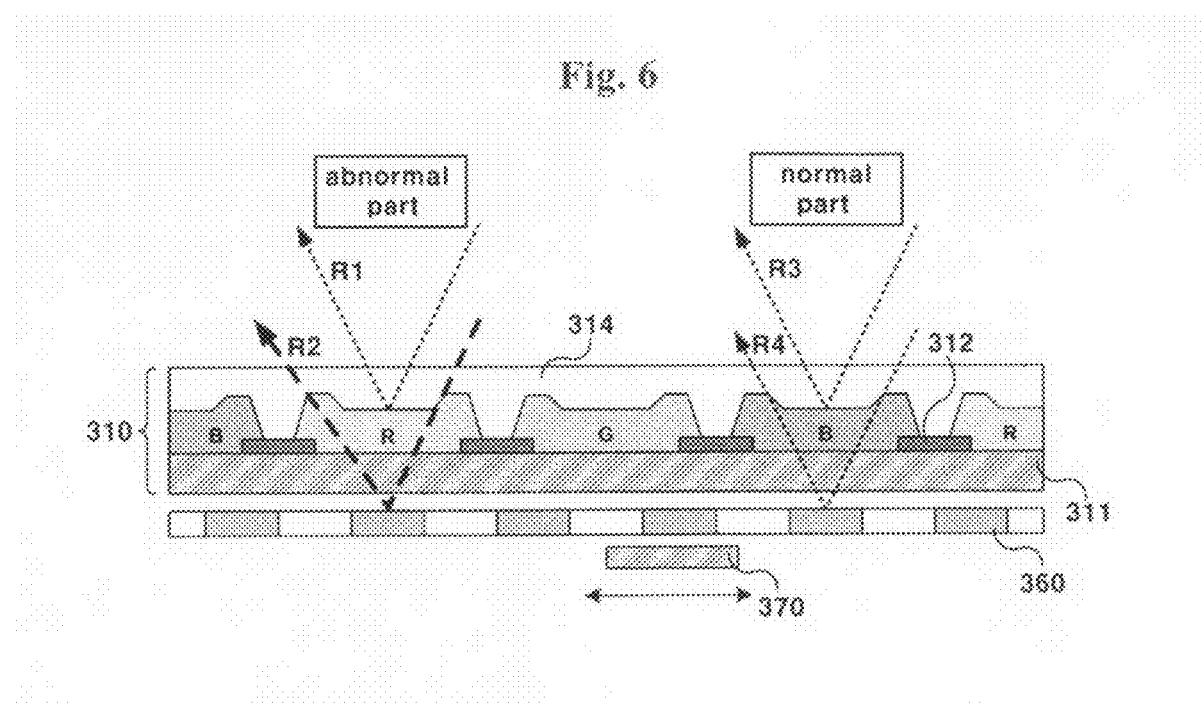

INSPECTING APPARATUS FOR GLASS SUBSTRATE

This nonprovisional application claims priority under 35 U.S.C. § 119(a) on Patent Application No. 2007-0030285 filed in Republic of Korea on Mar. 28, 2007, the entire contents of which are hereby incorporated by reference.

BACKGROUND OF THE INVENTION

1. Field of the Invention

This invention relates to an inspecting apparatus for a glass substrate to inspect whether a surface of a substrate is defective or not with naked eyes.

2. Related Art

In general, in fabricating a large-scale substrate such as semiconductor wafer or a liquid crystal display (LCD), a plasma display panel (PDP), an organic electro-luminescence display, and the like, the displays are inspected with naked eyes to detect debris, spots, or blurs that may remain on the substrates. In this case, an illumination device that uniformly illuminates the entirety of the substrate is used to facilitate detection of defects. The configuration of the related art inspecting apparatus for a glass substrate will now be described.

FIG. 1a is a view schematically showing the related art inspecting apparatus for a glass substrate, and FIG. 1b is a view substantially illustrating detection of light reflected by an upper illumination unit by an inspector.

First, with reference to FIG. 1a, the related art inspecting apparatus for a glass substrate comprises an upper illumination unit 30 and a rear illumination unit 40 which are, respectively, disposed at an upper side and a rear side of a glass substrate 10, an inspection target. An inspector 50 detects a defect of the glass substrate 10 by means of a reflective light L1 irradiated from the upper illumination unit 30 and a transmissive light L2 irradiated from the rear illumination unit 40. The glass substrate 10 is fixed by clampers 20 and comprises pattern regions such as a color filter region, a column spacer region, a pixel region, etc. formed on a front surface thereof. The inspector 50 is in front of the glass substrate 10 and checks whether the front surface of the glass substrate 10 is defective or not.

As shown in FIG. 1b, the upper illumination unit 30 comprises a light source 31, a reflecting unit 32, a condensing unit 33, and a scattering (diffusion) unit 34. When light is first generated from the light source 31, it is reflected to the condensing unit 33 by means of the reflecting unit 32, transmitted through the condensing unit 33 and the scattering unit 34, and then irradiated to the glass substrate 10, the inspection target. The light reflected by the glass substrate 10 proceeds to the naked eyes of the inspector 50. Then, the inspector 50 observes the reflected light to check whether the glass substrate 10 is defective or not.

The inspecting method is performed such that mura, namely, blurs, present on the glass substrate 10 is checked by the naked eyes of the inspector based on the difference between the strength and a reflection angle of light reflected from a flawless surface of the glass substrate 10 and those of light reflected from a defective surface of the glass substrate 10. However, the related art inspecting apparatus for the glass substrate has a problem in that, actually, it is not easy to properly inspect the glass substrate 10 because of the difference in thickness of pigments or an overlay in forming color filters. Namely, the pigments for forming red, green, and blue color filters, column spacers, or pixels of a TFT substrate make it difficult to detect blurs, such as overlay blurs, namely, butterfly blurs, that affect the characteristics of the viewing angle. For instance, the butterfly blurs can be detected, provided two or more layers are stacked, so after all the follow-up layer processes are performed, the butterfly blurs are inspected. In other words, the butterfly blurs cannot be detected until the follow-up layer processes are performed, resulting in a loss of production because the follow-up processes should be necessarily performed.

In an effort to solve this problem, pigments were formed or a pixel layered pattern was formed on a metal-deposited glass substrate and then a sampling inspection was performed. However, in case of using the metal-deposited glass substrate such as a TFT gate pattern, the blurs with respect to the pixels, the column spacers or the pigments of the color filters can be well seen, but disadvantageously, the sampling and the glass substrate should be separately fabricated, causing much loss in terms of production and costs.

BASIC SUMMARY OF THE INVENTION

An object of this invention is to provide an inspecting apparatus for a glass substrate capable of effectively detecting blurs (spots) generated on a green color filter layer, a blue color filter layer, a column spacer layer, a thin film transistor (TFT) layer, and so on, which have not been possibly inspected because of pigments used for fabricating a liquid crystal display (LCD) and structural weaknesses.

Another object of this invention is to provide an inspecting apparatus for a glass substrate capable of effectively detecting blurs (spots) of stacked layers caused by a thickness difference or overlay of pigments or blurs (spots) sensitive to light scattering (diffusion) characteristics to thus improve a production yield and quality of an LCD.

In an aspect, an inspecting apparatus for a glass substrate includes: a first illumination unit supplying reflective light to a surface of the substrate to inspect whether the surface of the substrate is defective or not; a second illumination unit supplying transmissive light from a rear side of the substrate to inspect whether the interior of the substrate is defective or not; a rear plate provided on a rear surface of the substrate; and a driving guide disposed on a rear surface of the rear plate and generating a phase difference between the light provided from the first illumination unit and the light provided from the second illumination unit. The driving guide may move up and down (vertically) or left and right (horizontally) along the rear surface of the rear plate, and interfere with or scatter (diffuse) light provided from the first and second illumination units if the glass substrate is defective.

In another aspect, an inspecting apparatus for a glass substrate includes: a first illumination unit supplying reflective light to a surface of the substrate to inspect whether the surface of the substrate is defective or not; a second illumination unit that supplies transmissive light from a rear side of the substrate to inspect whether the interior of the substrate is defective or not; and a rear plate disposed on a rear surface of the substrate and generating a phase difference between the light provided from the first illumination unit and the light provided from the second illumination unit. The rear plate may move up and down (vertically) or left and right (horizontally) along the rear surface of the rear plate, and interfere with or scatter (diffuse) light provided from the first and second illumination units if the glass substrate is defective.

BRIEF DESCRIPTION OF THE DRAWINGS

The implementation of this document will be described in detail with reference to the following drawings in which like numerals refer to like elements.

FIG. 2b is a view showing a mura defect that may be detected in inspecting the substrate.

FIG. 3 is a view for explaining a driving principle of the inspecting apparatus for a glass substrate according to a first embodiment of the invention.

FIG. 4 is view for explaining a principle for detecting blurs existing on the glass substrate by using the inspecting apparatus according to the first embodiment of the invention.

FIG. 5 is a view for explaining a driving principle of the inspecting apparatus for a glass substrate according to a second embodiment of the invention.

FIG. 6 is view for explaining a principle for detecting blurs existing on the glass substrate by using the inspecting apparatus according to the second embodiment of the invention.

DETAILED DESCRIPTION OF THE PREFERRED EMBODIMENTS

Figure 1A:
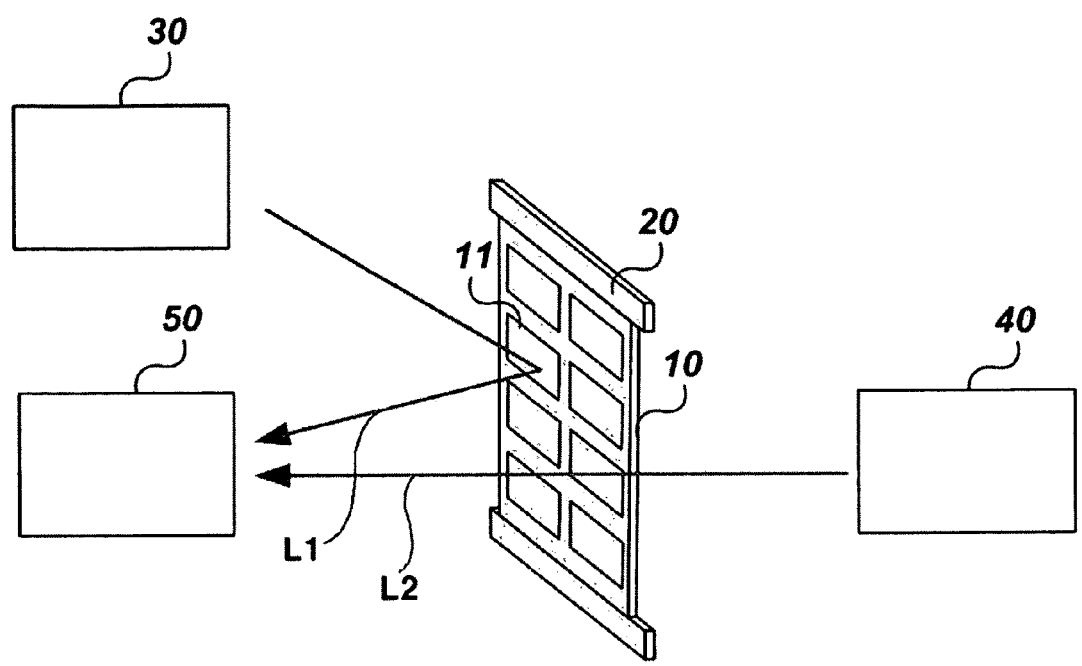
FIG. 1a is view schematically illustrating an inspecting apparatus for a glass substrate according to the related art.
Figure 1B:
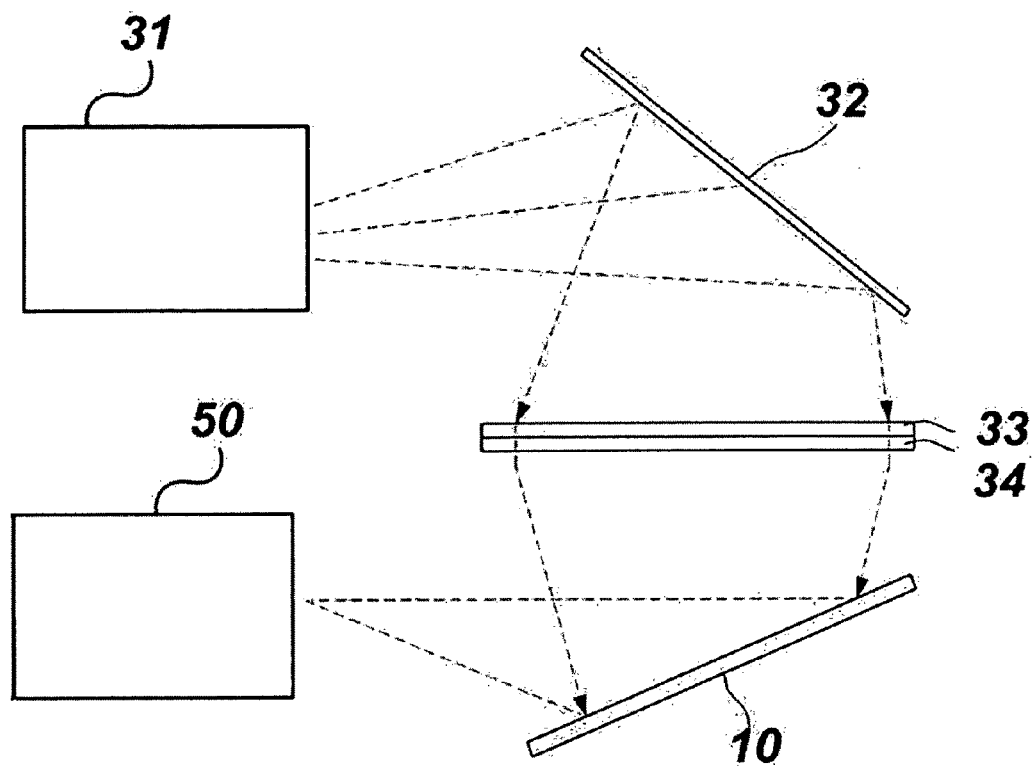
FIG. 1b is a view substantially illustrating detection of light reflected by an upper illumination unit by an inspector.

The foregoing and other objects, features, aspects and advantages of the invention will become more apparent from the following detailed description of the invention when taken in conjunction with the accompanying drawings. The same reference numerals denote the same elements throughout the specification.

The inspecting apparatus for a glass substrate according to the embodiments of the invention will now be described with reference to the accompanying drawings.

The invention provides a structure for remarkably improving mura detection capabilities of an inspecting apparatus for a glass substrate, namely, of a macro-inspecting apparatus for inspecting unspecified defects of a surface of the glass substrate.

Figure 2A:
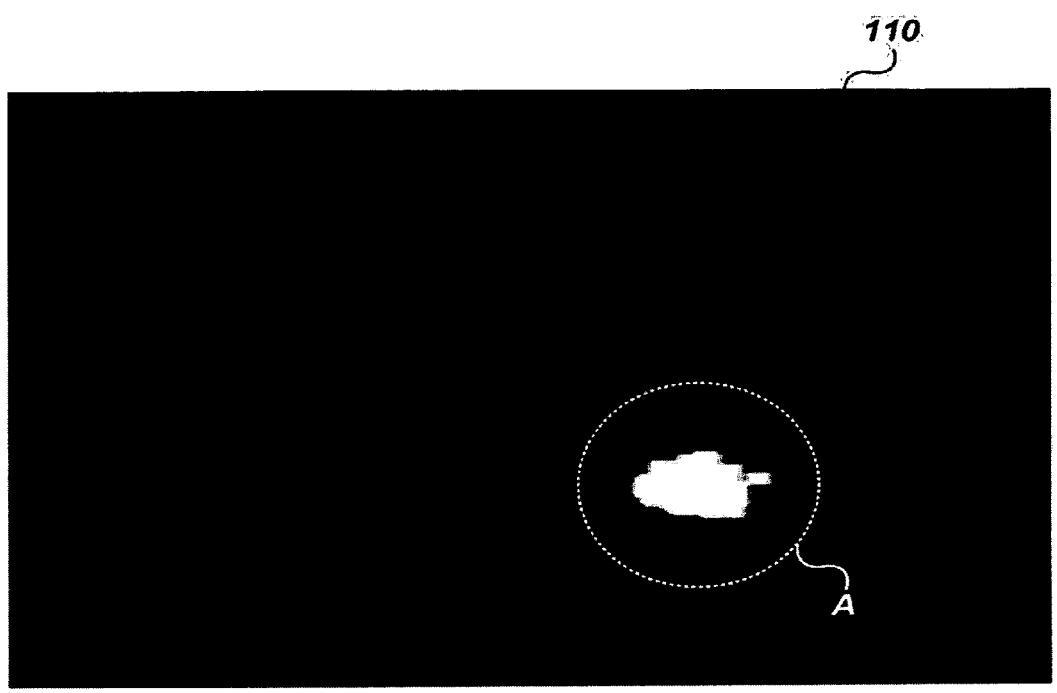
FIG. 2a is a plan view showing an inspecting apparatus for a glass substrate to which this document is applied.

FIG. 2a is a plan view showing an inspecting apparatus for a glass substrate to which this document is applied, and FIG. 2b is a view showing a mura defect that may be detected in inspecting the substrate.

As shown in FIG. 2a, the inspecting apparatus for a glass substrate according to the embodiments of the invention can easily detect an overlay blur of patterns or a mura defect generated due to a thickness difference of the patterns by using hologram light and polarization characteristics implemented by a rear plate 300 with a lattice pattern and a driving interferometer system 400.

Here, the rear plate 300 may be disposed on a rear surface of a glass substrate 100, an inspection target, and serve to fixedly clamp the glass substrate 100.

The rear plate 300 has the lattice pattern and may also serve as a surface plate chuck for adsorbing the glass substrate 100 in a vacuum state.

The driving interferometer system 400 may generate a phase difference of light irradiated to the rear plate 300. As shown, the driving interferometer system 400 may be provided in a plate form on the rear surface of the rear plate 300, and generates a phase difference of light while being moved vertically or horizontally, or may generate a phase difference of light by moving the rear plate 300 vertically or horizontally.

In this manner, the driving interferometer system 400 may be divided into two types according to its driving method for generating the phase difference of light.

In the inspecting apparatus for a glass substrate according to the embodiments of the invention, when light, which is to be irradiated to the glass substrate 100, passes through the rear plate 300, it is reflected by the rear plate 300. At this time, the reflective light reflected by the glass substrate 100 and the reflective light reflected by the rear plate 300 are interfered with each other due to their phase difference to generate hologram light.

In general, refractive index of light varies depending on types of media through which the light transmits. Thus, the reflection angle of the light reflected by a layer on the glass substrate 100 and that reflected by the rear plate 300 are different from each other, thereby making the phase difference therebetween.

The optical interference due to the phase difference may occur due to blurs or a thickness difference of pattern regions such as a color filter formation layer, a column spacer formation layer, a TFT formation layer, or the like, on the glass substrate 100, and the hologram light may appear like a rainbow pattern due to the optical interference as shown in FIG. 2b. Thus, the mura defect existing on the glass substrate 100 can be detected.

Compared with the related art inspecting apparatus for a glass substrate that allows observation of only the reflected light on the surface of the substrate, the inspecting apparatus for a glass substrate according to the embodiments of the invention employs the rear plate 300 which reflects light incident on the surface and the driving interferometer system 400 which moves a separate driving guide on the rear side of the rear plate 300 or moves the rear plate 300. That is, by using the phase difference between the reflective light from the surface of the glass substrate 100 and the reflective light by the rear plate 300 and the driving interferometer system 400, the defect detection capabilities with respect to the blurs resulting from the overlay, namely, the butterfly blurs due to the overlap of pixels can be enhanced.

The embodiments of the invention will now be described based on the two types of driving methods of the interferometer system 400.

A First Embodiment

FIG. 3 is a view for explaining a driving principle of the inspecting apparatus for a glass substrate according to a first embodiment of the invention, and FIG. 4 is view for explaining a principle for detecting blurs existing on the glass substrate by using the inspecting apparatus according to the first embodiment of the invention.

The inspecting apparatus for a glass substrate according to the first embodiment of the invention has such a structure that the driving interferometer system 400 for generating a light phase difference is provided on the rear surface of the rear plate.

First, with reference to FIG. 3, the inspecting apparatus for a glass substrate according to the first embodiment of the invention comprises an upper illumination unit 330 that provides a reflective light source to the surface of the glass substrate 310 to be inspected, a rear illumination unit 340 that provides a transmissive light source from a rear side of the glass substrate 310, a rear plate 360 provided on a rear surface of the glass substrate 310, and a driving guide 370 provided on a rear surface of the rear plate 360.

The glass substrate 310 is fixed to the rear plate 360 by means of clampers 320 and comprises pattern region 310a such as a plurality of color filter regions, column spacer regions, pixel regions for forming TFTs, and the like, formed on a front surface of the glass substrate 310.

The glass substrate 310 may be a color filter substrate for use in a liquid crystal display (LCD) comprising red, green, and blue color filters.

The upper illumination unit 330 may be installed at an upper side of the glass substrate 310 and provides a reflective light source to the surface of the glass substrate 310 to inspect a defect that may exist on the surface of the glass substrate 310.

The upper illumination unit 330 may comprise a light source (not shown), a reflecting unit (not shown), a condensing unit (not shown), and a scattering (diffusion) unit (not shown).

The light source generates light to be irradiated on the surface of the glass substrate 310. The reflecting unit reflects light generated from the light source to change a path of the light to the condensing unit. The condensing unit condenses light irradiated from the reflecting unit. The scattering unit allows light to be transmitted therethrough as it is or scattered according to whether or not power is applied, to thus facilitate detection of blurs of the glass substrate 310.

The rear illumination unit 340 is positioned at a rear side of the glass substrate 310, and irradiates a transmissive light to the surface of the glass substrate 310 to inspect whether the interior of the glass substrate 310 is defective or not.

The rear illumination unit 340 comprises a light source for generating the transmissive light, and the light source of the rear illumination unit 340 is provided to be moved in a forward/backward direction of the glass substrate 310.

The reason of driving the light source of the rear illumination unit 340 in the forward/backward direction is as follows.

As the glass substrate 310, the inspection target, is enlarged in size, the rear illumination unit 340 should be separated by more than a certain distance from the glass substrate 310 to secure a rotation radius of the glass substrate 310. In this respect, however, when the rear illumination unit 340 is separated by more than the certain distance from the glass substrate 310, the illuminance relatively is weakened in inspecting the interior of the glass substrate 310 as to whether it is defective or not. Thus, the light source needs to come closer to the glass substrate 310 to inspect the glass substrate 310, for which, thus, the light source of the rear illumination unit 340 is provided to be movable in the forward/backward direction.

The rear plate 360 has the lattice form and a reflection plate disposed on the rear surface of the glass substrate 310 to reflect light outputted from the rear surface of the glass substrate 310.

For instance, if the glass substrate 310 is a color filter substrate, the rear plate 360 would serve to reflect light which has passed through pigments that form the color filters after being provided from the upper illumination unit 330, so that blurs generated due to the thickness difference of the pigments can be detected.

The rear plate 360 may be made of a metallic material and have high transmittance and high reflectance in terms of its material characteristics. Specifically, the metallic material may be aluminum (Al) or chromium (Cr), etc.

The lattice pattern of the rear plate 360 may have various sizes. But in order to detect blurs and thickness difference of the pixel regions that form the TFTs as well as the multiple color filter regions and column spacer regions, the rear plate 360 may have a size equivalent to the region where the gate pattern of the TFT is formed.

The rear plate 360 is fastened to the glass substrate 310 by means of the clampers 320, and in this case, the rear plate 360 may be fastened to the glass substrate 310 with a certain distance therebetween or may be tightly attached to the glass substrate 310.

In addition, the rear plate 360 may also serve as a surface plate chuck that adsorbs the glass substrate 310 to be inspected in a vacuum state.

The driving guide 370 may be disposed on a rear surface of the rear plate 360 to generate a phase difference between light provided from the upper illumination unit 330 and that provided from the rear illumination unit 340.

The driving guide 370 may be moved up and down (vertically) or left and right (horizontally), may have a plate shape, and may be made of the metallic material such as the rear plate 360.

For example, the driving guide 370 may comprise a first driving guide 370a that is moved horizontally along the rear surface of the rear plate 360 and a second driving guide 370b that is moved vertically along the rear surface of the rear plate 360.

Light irradiated to the first driving guide 370a and the second driving guide 370b proceeds to the rear plate 360 and is then reflected to the glass substrate 310, and at this time, the light is interfered and scattered because of the vertical or horizontal movement of the first and second driving guides 370a and 370b.

Here, the light irradiated to the first and second driving guides 370a and 370b is provided by the upper illumination unit 330 and the rear illumination unit 340. In particular, the light provided from the upper illumination unit 330 is light which has passed through the glass substrate 310 and the rear plate 360 after being provided from the upper illumination unit 330.

Accordingly, the inspecting apparatus for a glass substrate according to the first embodiment of the invention performs inspecting on the glass substrate 310 while moving the driving guide 370 vertically or horizontally along the rear surface of the rear plate 360 in a state that the glass substrate 310 is fixed to the rear plate 360 in the vacuum state.

If the glass substrate 310 is defective, as shown in FIG. 4, a reflective light R1 reflected by the glass substrate 310 and a reflective light R2 reflected by the rear plate 360 and the driving guide 370 have different phases, making the two lights interfered with each other to generate hologram light in the shape of rainbow, or the like.

If the glass substrate 310 is normal or flawless, there is no phase difference between a reflective light R3 reflected by the glass substrate 310 and a reflective light R4 reflected by the rear plate 360 and the driving guide 370, so there is no optical interference nor light scattering.

In this manner, a mura defect of the glass substrate 310 can be detected.

With reference to FIG. 4, if the glass substrate 310 is a color filter substrate, a plurality of black matrixes 312 are formed at uniform distance on a substrate 311, and red (R), green (G), and blue (B) pigments are formed to form color filters between the black matrixes 312.

In this case, the characteristics of the red (R), green (G), and blue (B) pigments may cause the overlay and the thickness difference of the pigments to create a mura defect, which, however, can be effectively detected in the manner as described above.

In addition, by observing the phenomenon of the pattern phase difference based on the latticed rear plate 360, the particular mura, which can be possibly inspected after layers are stacked, such as the butterfly blurs can be detected at an earlier stage.

In addition, a defect of a non-metallic layer such as the pixel layer of the TFT can be also detected.

According to the first embodiment of the invention, the same detection effect as that of the related art method that performs the sampling inspection by using the glass substrate with the gate metal pattern deposited thereon can be obtained, and moreover, the costs for fabricating the glass substrate and sampling can be reduced compared with the related art method.

The Second Embodiment

FIG. 5 is a view for explaining a driving principle of the inspecting apparatus for a glass substrate according to a second embodiment of the invention, and FIG. 6 is view for explaining a principle for detecting blurs existing on the glass substrate by using the inspecting apparatus according to the second embodiment of the invention.

With reference to FIG. 5, an inspecting apparatus for a glass substrate according to the second embodiment of the invention comprises an upper illumination unit 530 that provides a reflective light source to a surface of a glass substrate 510 to be inspected, a rear illumination unit 540 that provides a transmissive light source from a rear side of the glass substrate 510, and a rear plate 560 provided on a rear surface of the glass substrate 510.

The glass substrate 510 may be fixed on a frame of the inspecting apparatus by means of clampers 520, and comprise pattern regions 510a such as a plurality of color filter regions, column spacer regions, pixel regions for forming TFTs, or the like, on its front surface.

The glass substrate 510 may be a color filter substrate for use in an LCD comprising red (R), green (G), and blue (B) color filters.

The upper illumination unit 530 is installed at an upper side of the glass substrate 510 and provides a reflective light source to the surface of the glass substrate 510 to inspect whether the surface of the glass substrate 510 is defective or not.

The rear illumination unit 540 is positioned at a rear side of the glass substrate 510 and irradiates transmissive light to the rear surface of the glass surface 510 to inspect whether the interior of the glass substrate 510 is defective or not.

Here, the upper illumination unit 530 and the rear illumination unit 540 according to the second embodiment of the invention are the same as the upper illumination unit 330 and the rear illumination unit 340 as shown in FIG. 3 according to the first embodiment of the invention, so its description will be omitted.

The rear plate 560 according to the second embodiment of the invention may have a lattice form, may be disposed on the rear surface of the glass substrate 510, and reflect light outputted from the rear surface of the glass substrate 510. For example, if the glass substrate 510 is a color filter substrate, the rear plate 560 serves to reflect light which has passed through pigments for formation of color filters after being provided from the upper illumination unit 530, to detect blurs generated due to a thickness difference of the pigments.

Also, the rear plate 560 generates a phase difference between the light provided from the upper illumination unit 530 and the light provided from the rear illumination unit 540, to generate optical interference and light scattering.

For this purpose, the rear plate 560 may be made of a metallic material with high reflectance and transmittance, and may be configured to be moved up and down (vertically) or right and left (horizontally) along the rear surface of the glass substrate 510.

In this case, the rear plate 560 may be separated by about 10 cm from the glass substrate 510 and moved vertically or horizontally within the distance of 10 cm.

Specifically, the metallic material may be aluminum (Al) or chromium (Cr), etc.

The lattice pattern of the rear plate 560 may have various sizes, but in order to detect blurs and the thickness difference of the pixel regions that form the TFTs as well as at the multiple color filter regions and column spacer regions, the rear plate 560 may have a size equivalent to the region where the gate pattern of the TFT is formed.

Accordingly, in the second embodiment of the invention, without such a driving guide disposed on the rear surface of the rear plate as in the first embodiment of the invention, the rear plate 560 is separated by a certain distance from the glass substrate 510 and moved vertically or horizontally to inspect the glass substrate 510.

The inspecting operation is performed by using optical interference and light scattering, during which, as mentioned, the rear plate 560 is moved vertically or horizontally without using any driving guide.

That is, with reference to FIG. 6, if the glass substrate 510 is a color filter substrate, a plurality of black matrixes 512 are formed at uniform distance on a substrate 511, and red (R), green (G), and blue (B) pigments are formed between the black matrixes 512 to form the color filters.

In this case, if there is a defect due to an overlay and thickness difference according to the characteristics of the red (R), green (G), and blue (B) pigments, a reflective light R'1 reflected by the glass substrate 510 and a reflective light R'2 reflected by the rear plate 560 which is moved vertically or horizontally would have different phases, causing the two lights to be interfered with each other and scattered to generate hologram light having a rainbow shape or the like.

If, however, the glass substrate 510 is normal or flawless, there is no phase difference between a reflective light R'3 reflected by the glass substrate 510 and a reflective light R'4 reflected by the rear plate 560, so there is no optical interference nor light scattering.

Accordingly, the mura defect that may be present on the glass substrate 510 can be detected.

In this manner, a defect of the non-metallic layer such as the pixel layer of the TFT, as well as the particular mura defect according to the stacked structure such as the overlay blurs, can be detected at an earlier stage.

As described above, the inspecting apparatus according to the embodiments of the invention has the advantages in that whether the green color filter layer, the blue color filter layer, the column spacer layer, the TFT layer, or the like, is defective or not can be detected, compared with the related art in which it is not possible to inspect the green color filter layer, the blue color filter layer, the column spacer layer, the TFT layer, or the like, because of the pigments used for fabricating the LCD or its structural weaknesses.

In particular, the improvement of the detection capabilities with respect to blurs of the stacked layers and blurs sensitive to light scattering characteristics such as the blues due to the thickness difference or overlay of the pigments can lead to enhancement of the production yield and quality of the LCD.

Also, by effectively disposing the inspecting apparatus for a glass substrate according to the embodiments of the invention and the existing inspecting apparatus for a substrate, the detection capabilities can be further improved at a relatively low investment cost and the efficiency of a production line can be enhanced.

In addition, by improving the detection capability with respect to particular mura defects in the process of fabricating the LCD, the inspecting apparatus for a glass substrate according to the invention can be utilized for a process monitoring and inspecting process.

It will be apparent to those skilled in the art that various modifications and variation can be made in the invention without departing from the spirit or scope of the invention. Thus, it is intended that the invention cover the modifications and variations of this invention provided they come within the scope of the appended claims and their equivalents.

What is claimed is:

1. An inspecting apparatus for a glass substrate comprising:
   a first illumination unit supplying reflective light to a surface of the substrate to inspect whether the surface of the substrate is defective or not;
   a second illumination unit supplying transmissive light from a rear side of the substrate to inspect whether the interior of the substrate is defective or not;
   a rear plate provided on a rear surface of the substrate; and
   a driving guide disposed on a rear surface of the rear plate and generating a phase difference between the light provided from the first illumination unit and the light provided from the second illumination unit.

2. The apparatus of claim 1, wherein the driving guide moves vertically or horizontally along the rear surface of the rear plate, and interferes with or scatters light provided from the first and second illumination units if the glass substrate is defective.

3. The apparatus of claim 2, wherein the driving guide comprises:
   a first driving guide moved horizontally along the rear surface of the rear plate; and
   a second driving guide moved vertically along the rear surface of the rear plate.

4. The apparatus of claim 1, wherein the substrate may comprise one of a color filter substrate and a thin film transistor substrate.

5. The apparatus of claim 1, wherein the rear plate has a lattice pattern and reflects light which has passed through the substrate after being provided from the first illumination unit.

6. The apparatus of claim 5, wherein the rear plate is made of one of aluminum (Al) and chromium (Cr).

7. The apparatus of claim 1, wherein the rear plate is a surface plate chuck absorbing the substrate in a vacuum state.

8. The apparatus of claim 1, further comprising:
   a clamper fixing the substrate to the rear plate.

9. The apparatus of claim 1, wherein the rear plate is tightly attached to the substrate.

10. An inspecting apparatus for a glass substrate comprising:
    a first illumination unit supplying reflective light to a surface of the substrate to inspect whether the surface of the substrate is defective or not;
    a second illumination unit supplying transmissive light from a rear side of the substrate to inspect whether the interior of the substrate is defective or not; and
    a rear plate disposed on a rear surface of the substrate and generating a phase difference between the light provided from the first illumination unit and the light provided from the second illumination unit.

11. The apparatus of claim 10, wherein the rear plate moves vertically or horizontally along the rear surface of the rear plate, and interferes with or scatters light provided from the first and second illumination units if the glass substrate is defective.

12. The apparatus of claim 11, wherein the rear plate is separated within the range of 10 cm from the substrate and moved vertically or horizontally.

13. The apparatus of claim 10, wherein the glass substrate to be inspected comprises one of a color filter substrate and a thin film transistor substrate.

14. The apparatus of claim 13, wherein the rear plate comprises a lattice pattern and reflects light which has passed through the substrate after being provided from the first illumination unit.

15. The apparatus of claim 14, wherein the rear plate is made of one of aluminum (Al) and chromium (Cr).

16. The apparatus of claim 10, further comprising:
    a clamper fixing the substrate to be inspected and the rear plate.

* * * * *